US006730496B2

(12) United States Patent
Edberg

(10) Patent No.: US 6,730,496 B2
(45) Date of Patent: *May 4, 2004

(54) METHOD OF DETECTING FIRST GENERATION ENVIRONMENTAL-SOURCED MICROBES IN AN ENVIRONMENTALLY-DERIVED SAMPLE

(76) Inventor: Stephen C. Edberg, 356 Woodland La., Orange, CT (US) 06477

( * ) Notice: Subject to any disclaimer, the term of this patent is extended or adjusted under 35 U.S.C. 154(b) by 0 days.

This patent is subject to a terminal disclaimer.

(21) Appl. No.: 10/036,288

(22) Filed: Oct. 24, 2001

(65) Prior Publication Data

US 2003/0190694 A1 Oct. 9, 2003

Related U.S. Application Data

(60) Division of application No. 09/114,464, filed on Jul. 13, 1998, now Pat. No. 6,329,166, which is a division of application No. 08/465,010, filed on Jun. 5, 1995, now Pat. No. 5,780,529, which is a continuation of application No. 08/323,064, filed on Oct. 14, 1994, now Pat. No. 5,429,933, which is a continuation of application No. 08/149,706, filed on Nov. 9, 1993, now abandoned, which is a continuation of application No. 07/824,893, filed on Jan. 22, 1992, now abandoned, which is a continuation of application No. 07/752,996, filed on Sep. 3, 1991, now abandoned, which is a continuation of application No. 07/349,653, filed on May 10, 1989, now abandoned, which is a continuation-in-part of application No. 06/880,305, filed on Jun. 30, 1986, now Pat. No. 4,925,789.

(51) Int. Cl.$^7$ ............................................. C12Q 1/10

(52) U.S. Cl. ............................ 435/34; 435/19; 435/38

(58) Field of Search ............................ 435/34, 19, 38, 435/802, 968; 436/63, 166, 172

(56) References Cited

U.S. PATENT DOCUMENTS

| | | | |
|---|---|---|---|
| 3,206,317 A | 9/1965 | Golber | |
| 3,496,066 A | 2/1970 | Berger et al. | |
| 3,870,601 A | 3/1975 | Warren et al. | |
| 4,129,483 A | 12/1978 | Bochner | |
| 4,208,480 A | 6/1980 | D'Amato et al. | |
| 4,235,964 A | 11/1980 | Bochner | |
| 4,245,043 A | 1/1981 | Lund | |
| 4,591,554 A | 5/1986 | Koumura et al. | |
| 4,622,297 A | 11/1986 | Kappner et al. | |
| 4,675,289 A | 6/1987 | Kanou et al. | |
| 4,803,162 A | 2/1989 | Smith et al. | |
| 4,812,409 A | 3/1989 | Babb et al. | 435/7 |
| 4,837,154 A | 6/1989 | Spiegel | 435/253.6 |
| 4,925,789 A | 5/1990 | Edberg | 435/38 |
| 5,004,684 A | 4/1991 | Simpson et al. | |
| 5,242,805 A | 9/1993 | Naleway | 435/18 |
| 5,292,644 A | 3/1994 | Berg | |
| 5,393,662 A | 2/1995 | Roth et al. | |
| 5,429,933 A | 7/1995 | Edberg | |
| 5,605,812 A | 2/1997 | Zomer | 435/38 |
| 5,610,029 A | 3/1997 | Ehrenfeld | 435/34 |
| 5,620,865 A | 4/1997 | Chen | 435/34 |
| 5,633,144 A | 5/1997 | Bitton | 435/38 |

FOREIGN PATENT DOCUMENTS

| | | |
|---|---|---|
| DE | 3419327 | 5/1984 |
| EP | 0025467 | 9/1979 |
| EP | 0059645 | 3/1982 |
| EP | 0332752 | 9/1989 |
| GP | 2005410 | 9/1978 |

OTHER PUBLICATIONS

Jul. 15, 2002 C.A.F.C. Ruling on appeal from the grant of C.P.I.–The Alternative Supplier, Inc.'s Motion for Summary Judgement of Non infringement of Edberg's U.S. Patents 5,780,259 and 5,429,933.
Nov. 24, 1997 Markman Ruling relating to U.S. Patent No.: 4,925,789; Environetics, Inc. et al. V. Millipore Corp.
Jun. 4, 2001 Ruling on Cross Motion for Summary Judgement relating to U.S. Patent Nos. 4,925,789; 5,429,933 and 5,780,259; Stephen C. Edberg, et al. V. CPI (3:98CV716).
Aug. 16, 2001 Ruling on Plaintiffs Motion for Reconsideration of the Jun. 4, 2001 Ruling.
"Bacteriological Ambient Water Quality Criteria for Marine and Fresh Recreational Waters", *Ambient Water Quality Criteria for Bacteria*, USEPA (1986).
Berg, et al., "Rapid Detection of Total and Fecal Coliforms in Water by Enzymatic Hydrolysis of 4–Methylumbelliferone–β–D–Galactoside," *Applied and Environmental Microbiology* 54:2118–2112 (1988).
Brenner, et al., "New Medium for the Simultaneous Detection of Total Coliforms and Escherichia coil in Water," *Applied and Environmental Microbiology* 59:3534–3544 (1993).
Cabelli, et al., "A Marine Recreation Water Quality Criterion Consistent with Indicator Concepts and Risk Analysis," *Journal WPCF* 55:1306–1314 (1983).
Cabelli, "Swimming–Associated Illness and Recreational Water Quality Criteria," *Wat. Sci. Tech.* 21:13–21 (1989).

(List continued on next page.)

Primary Examiner—Ralph Gitomer
(74) Attorney, Agent, or Firm—Kathleen M. Williams; Palmer & Dodge, LLP

(57) ABSTRACT

The invention relates to a method of detecting the presence or absence of a target microbe in a liquid sample, the method comprising: providing a powdered medium having one or more nutrient indicators and ingredients to support the growth of the target microbe, the one or more nutrient indicators being operable to alter a detectable characteristic in a medium/sample mixture when metabolized by the target microbes so as to confirm the presence or absence of target microbes in the sample, wherein the medium lacks a gelling agent and the medium is free of target microbes before mixing with a sample; providing a liquid sample; combining the powdered medium and the liquid sample to form a medium/sample mixture; and observing the mixture for the presence or absence of a detectable characteristic wherein the presence of the detectable characteristic results from a target microbe metabolizing a nutrient-indicator.

33 Claims, No Drawings

OTHER PUBLICATIONS

Dahlen and Linde, "Screening Plate Method for Detection of Bacterial β–Glucuronidase," *Applied Microbiology* 26:863–866 (1973).

Damare, et al., "Simplified Direct Plating Method for Enhanced Recovery of *Escherichia coli* on Food," *J. Food Science* 50:1736–1738 (1985).

DeMan, "The Probability of Most Probable Numbers," *European J. Appl. Microbiol* 1:67–78 (1975).

DIFCO Manual, 10$^{th}$ ed., DIFCO Laboratories, Detroit Michigan (1984).

Donnelly and Hartman, "Gentamicin–Based Medium for the Isolation of Group D Streptococci and Application of the Medium to Water Analysis," *Applied and Environmental Microbiology* 35:5786–581 (1978).

Edberg, et al., "National Field Evaluation of a Defined Substrate Method for the Simultaneous Enumeration of Total Coliforms and *Escherial coli* from Drinking Water: Comparison with Standard Multiple Tube Fermentation Method," *Applied and Environmental Microbiology* 54:1595–1601(1988).

Edberg and Kontnick, "Comparison of β–Glucuronidase–Based Substrate Systems for Identification of *Escheria coli*," *J. Clinical Microbiology* 24:368–371 (1986).

Feng and Hartman, "Fluorogenic Assays for Immediate Confirmation of *Escheria coli*," *Applied and Environmental Microbiology* 43:1320–1329(1982).

Gatti and Neviani, "A new Simple Medium for the Detection of *Enterococcus Faecalis* and *Enterococcus faecium* by Measurement of Conductance Changes" *Letters in Applied Microbiology* 17:72–74 (1993).

Hach Co. Catalog, p. 10, Loveland Colorado, May 1, 1986, Catalog Contained same items.

Hansen and Yourassowsky, "Detection of β–Glucuronidase in Lactose–Fermenting Members of the Family *Enterobacteriaceae* and Its Presence in Bacterial Urine Cultures," *J. Biol. Chem.* 20:1177–1179 (1984).

Hernandez, et al. "MPN miniaturized Procedure for the Enumeration of Faecal Enterococci in Fresh and Marine Waters: The Must Procedure," *Wat. Res.* 27:597–606 (1993).

Jay, *Modern Food Microbiology*, 4$^{th}$ ed., pp. 113–121 (1992).

Kendall, et al., "Observations of the Relative Constancy of Ammonia Production by Certain Bacteria," *J. Infectious Diseases* 13:425–428 (1913).

Kilian and Bulow, "Rapid Identification of Enterobacteriaceae," *Acta Path. Microbiol. Scand. Section B* 87:271–276 (1979).

Knutson and Hartman, "Comparison of Fluorescent Gentamicin–Thallous–Carbonate and KF Streptococcal Agars to Enumerate Enterococci and Fecal Streptococci in Meats", *Applied and Environmental Microbiology* 59:936–938 (1993).

Little and Hartman, "Fluorogenic Selective and Differential Medium for Isolation of Fecal streptococci," *Applied and Environmental Microbiology* 45:622–627 (1983).

Maddocks and Greenan, "Technical Method: A Rapid Method for Identifying Bacterial Enzumes," *J. Clinical Pathology* 23:686–687 (1975).

Mooney, et al. *Testing the Waters: A National Perspective on Beach Closings*, Natural Resources Defense Council, pp. 1–67 (1992).

Peeler, et al., "Chapter 6– The Most Probably Number Technique," *Compendium of Methods for the Microbiological Examination of Foods*, 3$^{rd}$ ed., pp. 105–120, Vanderzant and Splittstoesser eds., American Public Health Association (1992).

Robinson, B., "Evaluation of a Fluorogenic Assay for Detection of *Escheria coli* in foods," *Applied and Environmental Microbiology* 48: 285–288 (1984).

Sarhan and Foster, "A Rapid Fluorogenic Method for the Detection of *Escherichia coli* by the production of β–glucuronidase," *J. Applied Bacteriology* 70:394–400 (1991).

*Standard Methods for the Examination of Water and Waste Water*, 18$^{th}$ ed., Greenberg et al. eds, pp. 9–96 to 9–73 (1992).

*Standard Methods for the Examination of Water and Waste Water*, 18$^{th}$ ed., Greenberg et al. eds, pp. 9–45 to 9–64 (1992).

Thomas, "Bacterial Densities from Fermentation Tube Tests," *J. Am. Water Works Assoc.* 34:572–576 (1942).

Trepta and Edberg, "Esculinase (β–glucosidase) for the Rapid Estimation of Activity in Bacterial Utilizing a Hydrolyzable Substrate, p–nitropheny–β–D–glucopyranoside," *Antonie van Leeuwenhoek* 53:273–277 (1987).

Trepta and Edberg, "Methylumbelliferyl–β–D–Glucuronide–Based Medium for Rapid Isolation and Identification of *Escherichia coli*," *J. Clinical Microbiology* 19:172–174 (1984).

Ur and Brown, "Impedance Monitoring of Bacterial Activity," *J. Med. Microbiol.* 8:19–28 (1975).

METHOD OF DETECTING FIRST GENERATION ENVIRONMENTAL-SOURCED MICROBES IN AN ENVIRONMENTALLY-DERIVED SAMPLE

RELATED APPLICATIONS

This application is a divisional of U.S. Ser. No. 09/114,464, filed Jul. 13, 1998, now U.S. Pat. No. 6,329,166, which is a divisional of Ser. No. 08/465,010, filed Jun. 5, 1995, now U.S. Pat. No. 5,780,259, which is a continuation of U.S. Ser. No. 08/323,064 filed Oct. 14, 1994, now U.S. Pat. No. 5,429,933, which is a continuation of U.S. Ser. No. 08/149,706 filed Nov. 9, 1993, now abandoned, which is a continuation of U.S. Ser. No. 07/824,893 filed Jan. 22, 1992, now abandoned, which is a continuation of U.S. Ser. No. 07/752,996 filed Sep. 3, 1991, now abandoned, which is a continuation of U.S. Ser. No. 07/349,653 filed May 10, 1989, now abandoned, which is a continuation-in-part of U.S. Ser. No. 06/880,305 filed Jun. 30, 1986, now U.S. Pat. No. 4,925,789.

This invention relates to the detection of microbes in an environmental sample such as water, food, or the like. More particularly, this invention, relates to the detection of a target microbe through the use of a testing medium which medium contains a nutrient which can be significantly metabolized only by the target microbe during log phase of growth in the medium, and which, once metabolized, releases a moiety which alters a characteristic of the sample. The medium is thus a "specific medium" in that it will support growth in log phase of only the target microbes, rather than a general medium which will also support growth in log phase of microbes other than the target microbes. The medium also contains a growth accelerant for the target microbes to boost them through log phase and into log phase during the testing procedure. The microbes which this technique can detect are first generation environmental sample-sourced organisms.

In order to detect microbial pathogens in specimens, whether of human, animal or environmental origin, the following general procedure is commonly used: the target (and other) microbes in the specimen are, in the prior art, inoculated with the specimen into a culture medium in which they are provided with all the nutrients they require for growth. The specimen may be an untreated natural sample, or it may be a sample which has been pre-treated as, for example, by membrane filtration. The culture medium has the nutrients and other selective chemicals such as antimetabolites or antibiotics, which are selectively active against microbes other than the target microbes. The culture medium is a "general medium", even with the selective chemicals, in that it supports the growth of both target microbes and related microbes and thus is only partially specific to the target microbes.

The culture medium, which may be a water solution or a water gel, is sterilized to rid it of any contaminating microbes which may be present in the medium and which could, therefore, interfere with the analysis. The culture medium must be refrigerated and packaged in such a way to avoid contamination after manufacture.

After one or more of the culture media are inoculated with the specimen, the inoculated media are incubated under controlled atmospheric conditions. After incubation, the culture media are examined for growth of any microbes. If such growth is observed, a sample thereof is taken for further analysis, since the presence of the target microbe can only be established by isolating it in the pure state, not mixed with other microbes. Once isolated on subsequent culture media, the target microbes are identified by testing for a variety of physical and chemical characteristics. If the apparent target microbe growths are not isolated, false negative tests can result.

It will be readily appreciated that this most common analytical procedure is time consuming and must be carefully performed to preserve sterility.

This invention detects target microbes in a sample by using an indicator which is the preferred or primary nutrient for the target microbe, but which cannot be substantially metabolized by any other viable microbes which may be present in the sample along with the target microbe. The invention thus uses an active selector of the target microbes, rather than the passive reactors used by the prior art. The indicator will change a characteristic of the sample once the nutrient is metabolized by the target microbe. The characteristic can be: color (either visible, ultra violet, or infrared); electrical conductivity; electrical impedance; or the like. The preferred mode of performing the invention involves detecting the target microbes by use of a nutrient-indicator which, when metabolized, changes the visible or fluorescent color of an aqueous solution containing the specimen.

The nutrient-indicator actively participates in the growth of the target microbes by serving as the preferred or primary nutrient source. The target microbes can grow, metabolize and multiply into log phase, because they, and substantially only they, can use the indicator as their primary nutrient. Indicators can include chromogens attached to: salts; carbon; sulfur; amino acids; fatty acids; peptides; or other selective primary nutrients for microbes. Because microbes other than the target microbes are prevented from growing, metabolizing, or multiplying substantially into log phase, the medium is so specific that it does not have to be sterilized before use. Competition between target microbes and other microbes in the sample for the available primary nutrient in the medium is eliminated by the subject invention. The medium can be manufactured and packaged in a powder form which is added to the sample being tested. As noted, no sterilization is necessary. The medium can be dissolved in water and the sample can be added to the solution, or, if the sample is aqueous, the medium can be added directly to the sample.

The testing medium also includes a minor amount of a growth accelerant which will boost the target microbes and all of the other viable microbes in the sample through lag phase toward log phase of growth in the testing procedure. It will be understood by those skilled in the art that when a sample, such as environmental samples, are tested in accordance with the procedure of this invention, is combined with the testing medium of this invention, all of the microbes in the sample will lapse into a lag phase of growth, due to the newness of the environment they are in. In the lag phase, none of the microbes will significantly multiply and grow until they adjust to the new environment. This dormant stage, which all of the microbes, including the targets, encounter, causes the test period to be undesirably long. The growth accelerant which is incorporated into the medium of this invention is a combination of natural plant extracts, vitamins, and minerals which hasten the transition of the target microbes, and all of the other microbes in the sample, through the lag phase and into the log phase so as to lessen the time duration from the inception of the test to the alteration (or no alteration) of the sample which indicates the presence (or absence) of the target microbes in the sample. The total time lapse will be reduced by about one half by inclusion of the accelerant in the medium. The accelerant is present in a small amount so as to be dissipated by the time the microbes enter log phase of growth.

The development of a specific color indicates the presence of the target microbes. This may occur at any time after the procedure is initiated. There is no need to purify the target microbes. There is no need to perform any chemical analysis of the sample to determine whether the target microbes are present.

As used in this disclosure, the term "target microbe(s)" can refer to a single-microbe; a related species of microbes; or a large genus of microbes possessing a common taxonomic characteristic. The indicator only needs to be specific to the "target microbe". For example, indicators are available for detecting a single microbe, such as Escherichia coli (E. Coli), or for detecting any one of a closely related species of microbes, such Klebsiella-Enterobacter-Serratia, or any one of a large genus of microbes, such as Gram negative bacteria, for example. The chromogens used in the nutrient-indicator can produce color in the visible range; the ultraviolet range; or the infrared range. As will be appreciated from the aforesaid, the nutrient-indicator will preferably be colorless in the non-metabolized state, and will preferably release a color moiety after being metabolized by the target microbes. The color may be visible, fluorescent, machine-readable, or a combination of the aforesaid. As previously noted, using the invention, there is very little, or no, competition for food or nutrients among the microbes in the medium because the only nutrient present in the medium which can be metabolized to any significant extent, can be metabolized solely by the target microbes. Accordingly, a significant number of false-negative tests which will occur with the procedures of the prior art are eliminated by this invention. The nutrient used will be one that the target microbes greatly prefer over any other nutrients, and also, one for which other microbes in the sample have little or no preference, and cannot significantly assimilate. Thus, only the presence of the target microbes in the specimen can result in sufficient metabolism of the nutrient to cause the color, or other characteristic change, in the sample. This is the crux of the invention.

Since the nutrient-indicator is substantially specific only to the target microbes, and is the preferred, or primary, nutrient in the medium for the target microbes, the target microbes will be drawn to the nutrient-indicator, thus further speeding up the color change.

It is, therefore, an object of this invention to provide a procedure for detecting microbes in a specimen by metabolistically changing a detectable characteristic of the sample.

It is an additional object of this invention to provide a procedure of the character described wherein the color of the sample is changed by metabolization by a target microbe.

It is another object of this invention to provide a procedure of the character described wherein the color change is provided by metabolism by the target microbes, of a nutrient added to the sample, which nutrient includes a chromogenic moiety which is detectable only after the nutrient is metabolized.

It is a further object of this invention to provide a procedure of the character described wherein the nutrient having the chromogenic moiety can only be significantly metabolized by the target microbes.

It is another object of this invention to provide a procedure of the character described wherein the nutrient can only support growth or the target microbes in log phase, and the remaining viable microbes in the sample cannot sustain log phase of growth since they cannot metabolize the nutrient-indicator to the extent required therefor.

It is a further object of this invention to provide a procedure wherein the growth of the target microbes is accelerated into log phase to lessen the time period needed to conduct the test.

These and other objects of the invention will become more readily apparent from the following detailed description of several preferred embodiments thereof.

Three examples of the use of the invention to detect a genus and a species of gram negative microbe (Escherichia coli), a genus and species of gram positive microbe (Streptococcus faecalis), and a taxonomic class consisting of a large group containing many members (Gram negative microbes) are set forth hereinafter. When a specimen is examined for any of these three, each is referred to as the target microbe(s).

The nutrient is a substrate of the enzyme B-glucuronidase. If one wishes to determine the presence of E. coli by a color change, the nutrient-indicator can be orthonitrophenyl-B-D-glucuronide (yellow), B-napthalamide-B-D-glucuronide (purple), alpha-napthol-B-D-glucuronide (red), or methylumbilliferyl-B-D-glucuronide (fluorescent), or the like.

The nutrient-indicator serves as the essential source of carbon. The rest of the medium is tailored so that each ingredient provides a requirement for E. coli.

First, to prevent competition from microbes other than the broad category of Gram negative bacteria, the antibiotics vancomycin and ansiomycin are added in the percent by weight of 5%. These antibiotics may be present in the range of 1% to 10% by weight.

Second, to select E. coli from Gram negative bacteria, the following ingredients are used:

| INGREDIENT | SOURCE | % BY WEIGHT | RANGE % BY WEIGHT |
|---|---|---|---|
| Nitrogen | ammonium sulfate | 37. | 10–50 |
| Amino Acids | histidine | .0697 | 0.02–0.1 |
|  | methionine | .1860 | 0.02–0.4 |
|  | tryptophan | .2325 | 0.02–0.5 |
| Vitamins | biotin | .000232 | 0.0001–0.00 |
|  | pantothenate | .0093 | 0.001–0.03 |
|  | folic acid | .000232 | 0.0001–0.02 |
|  | inositol | 0186 | 0.01–0.02 |
|  | P-aminobenzoic acid | .046 | 0.01–.1 |
|  | pyrodoxine hydrochloride | .093 | 0.05–0.3 |
|  | riboflavin | .037 | 0.01–0.06 |
|  | thiamine | 0.37 | 01–0.06 |

| INGREDIENT | SOURCE | % BY WEIGHT | RANGE BY WEIGHT |
|---|---|---|---|
| Elements | fenic chloride | .046 | 0.02–0.1 |
|  | copper sulfate | .00186 | 0.001–0.002 |
|  | manganese sulfate | .0037 | 0.002–0.007 |
|  | potassium chloride | .00001 | 0.00001–0.001 |
|  | potassium iodide | .0000046 | 0.000001–0.00001 |
|  | zinc sulfate | .046 | 0.01–0.08 |
|  | boric acid | .460 | 0.01–0.5 |
|  | magnesium chloride | .019 | 0.01–0.05 |
| Salts | potassium phosphate monobasic | 9.0 | 1–15 |
|  | potassium phosphate | 23.0 | 2–30 |

| | -continued | |
|---|---|---|
| dibasic sodium carbonate | 23.0 | 2–30 |
| magnesium sulfate | 4.6 | 1–10 |
| sodium chloride | .9 | 0.2–5 |
| calcium chloride | .9 | 0.2–5 |
| sodium pyruvate | .023 | 0.01–0.1 |
| Nutrient-indicator | .345 | 0.2–2 |
| Accelerant | 2.0 | 1.5–2.5 |

*Streptococcus Faecalis*

*Streptococcus faecalis* is a microbe found to be a cause of urinary tract infection. It is the major bacterium sought out in swimming water.

The nutrient-indicator is a substrate of the enzyme L-pyronidonyl aminopeptidase. If one wishes to determine the presence of *Streptococcus faecalis* by a color change, the nutrient-indicator molecule can be orthonitrophenyl-B-L-pyronidonyl (yellow); B-napthalamide-B-L-pyronidonyl (purple); alpha-napthol-B-L-pyronidonyl (red); or methylumbilliferyl-B-L-pyronidonyl (fluorescent).

The nutrient-indicator serves as the essential source of carbon. The rest of the medium is tailored so that each ingredient provides a requirement for *S. faecalis*.

First, to prevent competition from microbes other than the broad category of Gram positive bacteria, the antibiotics colistin, naladixic acid and ansiomycin are added.

Second, to select *Streptococcus faecalis* from Gram positive bacteria, the same ingredient mixture specified for *E. coli* is used with the above-noted nutrient-indicator and antibiotics. The nutrient-indicator is present in a concentration of 0.345 percent by weight, the usable range being about 0.2 to about 2.0 percent by weight and the antibiotics are present in the concentration of 5 percent by weight, the usable range being about 1 to about 10 percent by weight.

Gram Negative Bacteria

There are two broad classes of bacteria; Gram positive and Gram negative. Gram negative bacteria are important because they contain a toxic material as part of their bodies called endotoxin. They also may contaminate pharmaceuticals and other medical preparations.

The nutrient-indicator is a substrate of the enzyme L-alanine aminopeptidase. If one wishes to determine the presence of Gram negative bacteria by a color change, the nutrient-indicator molecule can be L-alanine-B-orthonitrophenyl (yellow); B-napthalamide-B-L-alanine (purple); alpha-napthol-B-L-alanine (red); or methylumblillferyl-B-L-alanine (fluorescent).

The nutrient-indicator serves as the essential source of carbon. The rest of the medium is tailored so that each ingredient provides a requirement for Gram negative bacteria.

First, to eliminate microbes other than the broad category of Gram negative bacteria, the antibiotics ansiomycin (eliminates yeast) and vancomycin (eliminates Gram positives) are added in amounts of 5% by weight.

The same ingredient mixture specified above is used with the nutrient-indicator being present in the amount of 0.345% by weight and in the range of about 0.2 to about 2.0% by weight, and the antibiotics may be present in the range of about 1 to about 10% by weight.

In all of the aforesaid examples, the accelerant mixture of plant extracts, vitamins and minerals which can be assimilated by all of the microbes in the sample will be included in the amount of about 2% by weight.

A sample of the specimen is added to a vessel, such as a bottle. The testing medium of this invention is added to the specimen and well mixed. If the sample is a solid, a water diluent can be used. If the target microbe or group of microbes are present, the invention will change color (at any time from the time of inoculation). There is no technical time or labor required after inoculation of the invention. Also, because the end-point is a defined color change, it does not require a trained individual to determine positivity.

Substrates are available to specifically detect fecal coliforms (*E. coli*), total coliforms, the Klebsiella-Enterobacter-Serratia group; and *Streptococcus faecalis*.

This invention is particularly useful in analyzing water. When water is analyzed, if necessary, sodium thiosulfate or sodium EDTA may be added to neutralize antibacterials found in water.

To analyze water for *E. coli* by the invention, the following procedure is followed:

1. A water sample is collected using precalibrated pipettes: 1.0 milliliter; 0.1 milliliter; and 0.01 milliliter, from which amounts of the water sample are added to each of three tubes. The aforesaid medium of this invention is added in powder form (alternatively, the medium can be present in powder form in the tubes).
2. The tubes are incubated at between 20 degrees C. (70F.) to 44 degrees C. (140F.).
3. The presence of *E. coli* is indicated by the change in color in the tube.
4. If greater than 100 *E. coli*/ml are present, the 0.01 tube will be positive; if greater than 10 *E. coli*/ml are present, the 0.1 ml tube will be positive; if less than one *E. coli*/ml is present, only the 1 ml tube will be positive.

A positive test can occur anytime from shortly after inoculation with a heavily inoculated sample, to 20 hours, if there is only one target bacterium initially present per milliliter of sample. Whatever the time period needed to produce the color change, this time period will be substantially reduced by the accelerant which will boost the microbes into log phase growth. The only technical manipulation is the addition of the water to the tubes by the pre-calibrated pipettes.

The same medium described above was used to analyze water in the presence or absence (P-A) test for *E. coli*.

1. A 100 ml sample of water was added to a vessel containing the aforesaid medium of this invention.
2. If the reaction mixture changes color, *E. coli* is present and the test is positive.
3. Confirmatory or other tests are not necessary.

The procedure of this invention was tested with several B-glucuronidase and B-galactopyranoside substrates in the field. A comparison of the procedure of this invention in a P-A test format was made with the conventional membrane filtration technique, and was analyzed according to the EPA protocol for the certification of new devices. The procedure of this invention is specific and requires no confirmatory tests. The test was conducted for two target microbes; *E. coli*; and total coliforms. The base formula was made as described above; only the hydrolyzable substrate was changed for the detection of the particular target microbes.

In general, with respect to this invention, after the specific medium has been added to the sample, during the lag phase while the microbes are adjusting to the presence of the medium no substantial microbial metabolism will occur with either the target or non-target microbes. At the beginning of the log phase, all of the microbes will begin to metabolite the vitamin and mineral component of the medium, but only the target microbes will also metabolize the specific nutrient component of the medium. This specific nutrient is the only ingredient in the medium which will allow substantial growth, i.e., growth which will allow microbial reproduction at logarithmic rates (log phase), of any microbes in the sample. Thus, the medium will only support reproductive growth of the target microbes. For this reason the population of non-target microbes in the sample will not substantially increase, and will actually begin to decline during the log phase. By the time that the log phase has progressed to the equilibrium phase, the population growth rate of the target microbes will be at least ten times that of any other microbes in the sample due to the selective reproductive growth of the target microbes and the concurrent static, or declining, population of all other microbes in the sample. Commonly, in the log phase, the target microbe population growth rate will be ten thousand times or more, than that of any other microbes in the sample.

It will be readily appreciated that the specific medium of this invention can be produced in powder form and packaged in ready-to-use quantities specific to a variety of target microbes. The medium, as produced, can include antibiotic components, if desired.

Since many changes and variations of the disclosed embodiments of this invention may be used without departing from the inventive concept, it is not intended to limit the invention otherwise than as required by the appended claims.

What is claimed is:

1. A method of detecting the presence or absence of one or more target microbes in a liquid sample, said method comprising the steps of:
    a) providing a powdered medium having one or more nutrient indicators and ingredients to support the growth of said target microbe, said one or more nutrient indicators being operable to alter a detectable characteristic in a medium/sample mixture when metabolized by the target microbes so as to confirm the presence or absence of target microbes in the sample; wherein said medium lacks a gelling agent and said medium is free of target microbes before mixing with a sample;
    b) providing a liquid sample;
    c) combining said powdered medium and said liquid sample to form a medium/sample mixture; and
    d) observing the mixture for the presence or absence of said detectable characteristic wherein the presence of said detectable characteristic results from one or more target microbes metabolizing one or more of said nutrient-indicators.

2. The method of claim 1, wherein said liquid sample is a water sample.

3. The method of claim 1, wherein said liquid sample is an environmental sample.

4. The method of claim 1, wherein said liquid sample is a first generation water sample.

5. The method of claim 1, wherein said liquid sample is a natural water sample.

6. The method of claim 1, wherein said one or more nutrient indicators actively participates in the growth of said target microbe.

7. The method of claim 1, further comprising, after step (c), the step of incubating said medium/sample mixture at temperatures operable to support the growth of said target microbe.

8. The method of claim 1, wherein the population growth rate of said target microbe during log phase is at least 10 times that of any non-target microbe present in said sample.

9. The method of claim 1 wherein the population growth rate of said target microbe during log phase is at least 10,000 times that of any non-target microbe present in said sample.

10. The method of claim 1, wherein said detectable characteristic is a particular color of said medium/sample mixture.

11. The method of claim 1, wherein said detectable characteristic is fluorescence.

12. The method of claim 1, wherein said target microbe is fecal bacteria.

13. The method of claim 1, wherein said target microbe is coliform bacteria.

14. The method of claim 1, wherein said target microbe is *E. coli*.

15. The method of claim 1, wherein said nutrient indicator is a substrate for β-glucuronidase.

16. The method of claim 15, wherein said nutrient indicator is selected from the group consisting of: orthonitrophenyl-B-D-glucuronide; B-napthalamide-B-D-glucuronide; α-napthol-B-D-glucuronide; and methylumbelliferyl-B-D-glucuronide.

17. The method of claim 1, wherein said target microbe is *Streptococcus faecalis*.

18. The method of claim 1, wherein said nutrient indicator is a substrate for L-pyronidyl aminopeptidase.

19. The method of claim 18, wherein said nutrient indicator is selected from the group consisting of: orthonitrophenyl-B-L-pyronidyl; B-napthalamide-B-L-pyronidyl; α-napthol-B-L-pyronidyl; and methylumbelliferyl-B-L-pyronidyl.

20. The method of claim 1, wherein said target microbe is Gram negative bacteria.

21. The method of claim 1 wherein said nutrient indicator is a substrate of L-alanine aminopeptidase.

22. The method of claim 21 wherein said nutrient indicator is selected from the group consisting of: L-alanine-B-orthonitrophenyl; B-napthalamide-B-L-alanine; α-napthol-B-L-alanine; and methylumbelliferyl-B-L-alanine.

23. A method of detecting the presence or absence of one or more target microbes in a water sample, said method comprising the steps of:
    a) providing a powdered medium having one or more nutrient indicators and ingredients to support the growth of said target microbe, said one or more nutrient indicators comprising a substrate for β-glucuronidase which is operable to alter the color of a medium/sample mixture when metabolized by the target microbes so as to confirm the presence or absence of target microbes in the sample, wherein said one or more nutrient indicators actively participates in the growth of said target microbe, wherein said medium lacks a gelling agent and wherein said medium is free of target microbes before mixing with a sample;
    b) providing a water sample;
    c) combining said powdered medium and said water sample to form a medium/sample mixture; and
    d) observing the color of the mixture, wherein altered color results from one or more target microbes metabolizing said substrate for β-glucuronidase.

24. The method of claim 23, wherein said water sample is an environmental sample.

25. The method of claim 23, wherein said water sample is a first generation water sample.

26. The method of claim 23, wherein said water sample is a natural water sample.

27. The method of claim 23, further comprising, after step (c), the step of incubating said medium/sample mixture at temperatures operable to support the growth of said target microbe.

28. The method of claim 23, wherein the population growth rate of said target microbe during log phase is at least 10 times that of any non-target microbe present in said sample.

29. The method of claim 23 wherein the population growth rate of said target microbe during log phase is at least 10,000 times that of any non-target microbe present in said sample.

30. The method of claim 23, wherein said target microbe is fecal bacteria.

31. The method of claim 23, wherein said target microbe is coliform bacteria.

32. The method of claim 23, wherein said target microbe is *E. coli*.

33. The method of claim 23, wherein said nutrient indicator is selected from the group consisting of: orthonitrophenyl-B-D-glucuronide; B-napthalamide-B-D-glucuronide; α-napthol-B-D-glucuronide; and methylumbelliferyl-B-D-glucuronide.

* * * * *